US009636300B2

(12) United States Patent
Lee

(10) Patent No.: US 9,636,300 B2
(45) Date of Patent: *May 2, 2017

(54) RACECADOTRIL LIPID COMPOSITIONS

(71) Applicant: JOHNSON & JOHNSON CONSUMER INC., Skillman, NJ (US)

(72) Inventor: Der-Yang Lee, Flemington, NJ (US)

(73) Assignee: Johnson & Johnson Consumer Inc., Skillman, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/205,565

(22) Filed: Mar. 12, 2014

(65) Prior Publication Data

US 2014/0271832 A1    Sep. 18, 2014

Related U.S. Application Data

(60) Provisional application No. 61/787,597, filed on Mar. 15, 2013.

(51) Int. Cl.
| | |
|---|---|
| *A61K 31/216* | (2006.01) |
| *A61K 31/222* | (2006.01) |
| *A61K 45/06* | (2006.01) |
| *A61K 47/14* | (2006.01) |
| *A61K 9/107* | (2006.01) |
| *A61K 9/48* | (2006.01) |
| *A61K 47/44* | (2017.01) |

(52) U.S. Cl.
CPC .......... *A61K 9/1075* (2013.01); *A61K 9/4858* (2013.01); *A61K 31/216* (2013.01); *A61K 31/222* (2013.01); *A61K 45/06* (2013.01); *A61K 47/14* (2013.01); *A61K 47/44* (2013.01)

(58) Field of Classification Search
CPC .... A61K 31/216; A61K 31/222; A61K 45/06; A61K 47/14; A61K 47/44; A61K 9/1075; A61K 9/4858
See application file for complete search history.

(56) References Cited

U.S. PATENT DOCUMENTS

| | | | |
|---|---|---|---|
| 4,513,009 | A | 4/1985 | Roques et al. |
| 5,136,076 | A | 8/1992 | Duhamel et al. |
| 5,208,255 | A | 5/1993 | Duhamel et al. |
| 5,296,509 | A | 3/1994 | Duhamel et al. |
| 5,331,008 | A | 7/1994 | Duhamel et al. |
| 6,919,093 | B2 | 7/2005 | Lecomte et al. |
| 8,222,294 | B2 | 7/2012 | Schwartz et al. |
| 8,318,203 | B2 | 11/2012 | Schwartz et al. |
| 2002/0028248 | A1 | 3/2002 | Tsukada et al. |
| 2009/0186084 | A1* | 7/2009 | Schwartz et al. ............ 424/474 |
| 2013/0331423 | A1 | 12/2013 | Julien et al. |
| 2014/0005261 | A1 | 1/2014 | Lee et al. |
| 2014/0005262 | A1 | 1/2014 | Lee |
| 2014/0271831 | A1 | 9/2014 | Lee |
| 2014/0271832 | A1 | 9/2014 | Lee |
| 2014/0274948 | A1 | 9/2014 | Lee et al. |
| 2015/0342882 | A1 | 12/2015 | Lee |

FOREIGN PATENT DOCUMENTS

| | | | |
|---|---|---|---|
| CN | 101264065 | A | 9/2008 |
| CN | 101442990 | A | 5/2009 |
| CN | 102018707 | A * | 4/2011 |
| CN | 102133186 | A | 7/2011 |
| EP | 1563848 | A1 * | 8/2005 |
| EP | 2462922 | A | 6/2012 |
| EP | 2749270 | A1 | 7/2014 |
| IN | 20060165213 | | 7/2008 |
| IN | 20080088413 | | 11/2011 |
| IN | 201101191211 | | 10/2012 |
| IN | 20110127411 | A1 | 11/2012 |
| IN | 20110127511 | | 11/2012 |
| WO | WO 98/40051 | | 9/1998 |
| WO | WO 00/59482 | A1 | 10/2000 |
| WO | WO 2001/097803 | A1 | 12/2001 |
| WO | WO 2005/079850 | A1 | 9/2005 |
| WO | WO 2011/002702 | A1 | 1/2011 |
| WO | WO 2014/005032 | A1 | 1/2014 |
| WO | WO 2014/150660 | A1 | 9/2014 |
| WO | WO 2015/100234 | A1 | 7/2015 |

OTHER PUBLICATIONS

John B. Cannon (American Pharmaceutical Review, May 2011).*
Zargar-Shoshtari et al. (Chem. Pharm. Bull. 58(10) 1332-1338 (2010)).*
Mukherjee et al ("Mukherjee", JPP 2010, 62: 1112-1120).*
EPO machine translation of CN102018707A.*
Kaplan et al. ("Kaplan", Arch. Fam. Med, 1999, 8, p. 243-248).*
U.S. Appl. No. 14/205,565, Racecadotril lipid compositions, U.S. Appl. No. 61/787,597, 1. A composition comprising: racecadotril, at least one surfactant and a lipid. Markush group for surfactant and Markush group for lipid included in claim 1, Awaiting examination.
U.S. Appl. No. 14/138,309, Racecadotril microemulsion compositions, U.S. Appl. No. 13/929,996, U.S. Appl. No. 61/787,597, U.S. Appl. No. 61/665,470, 1. A composition comprising: racecadotril, at least one surfactant, wherein the surfactant is selected from polyoxyl 35 castor oil, glyceryl caprylate (mono- and diglycerides), and combinations thereof, and a lipid, wherein the lipid is a medium chain triglyceride, Awaiting examination.
U.S. Appl. No. 13/929,996, Racecadotril lipid composition, U.S. Appl. No. 61/787,597, U.S. Appl. No. 61/665,470, 1. A composition comprising: racecadotril, at least one surfactant and a lipid, Response to Restriction Requirement filed Jun. 9, 2014. Elexted composition claims. Response to non-final Office Action due Nov. 14, 2014.
U.S. Appl. No. 14/205,534, Racecadotril liquid compositions, U.S. Appl. No. 61/787,496, 1. A liquid composition comprising racecadotril and cyclodextrin, wherein the cyclodextrin is a sulfobutyl ether derivative of β-cyclodextrin, Response to non-final Office Action filed Sep. 3, 2014.
U.S. Appl. No. 14/138,272, Racecadotril liquid compositions, U.S. Appl. No. 13/929,975 U.S. Appl. No. 61/787,496, 1. A liquid composition comprising racecadotril and cyclodextrin. Response to non-final Office Action due Nov. 13, 2014. Claim to be amended in order to distinguish from claims in U.S. Appl. No. 13/929,975 will be filed with response.
U.S. Appl. No. 13/929,975, Racecadotril lipid compositions, U.S. Appl. No. 61/665,458 U.S. Appl. No. 61/787,496, 1. A liquid composition comprising racecadotril and cyclodextrin. Response to non-final office action filed Jun. 9, 2014.

(Continued)

*Primary Examiner* — Ernst V Arnold
(74) *Attorney, Agent, or Firm* — Laura A. Donnelly

(57) ABSTRACT

A composition comprising racecadotril, at least one surfactant and a lipid.

15 Claims, No Drawings

(56) References Cited

OTHER PUBLICATIONS

International Search Report for PCT/US2014/023903 dated Jul. 14, 2014.
International Search Report for PCT/US2013/048593 dated Sep. 19, 2013.
Cannon (American Pharmaceutical Review, May 2011).
Laddha et al. (Brazillian Journal of Pharmaceutical Sciences (Impresso), vol. 50, No. 1 (2014).
Mukherjee et al. (JPP 2010, 62: 1112-1120).
Zargar-Shoshtari et al. (Chem. Pharm. Bull. 58(10) 1332-1338 (2010).
Monali, Yeole et al: "Development and Evaluation of Poorly Aqueous Soluble Drug Racecadotril by Using Solid Self Micro Emulsifying Drug Delivery Approach", International Research of Pharmacy. vol. 5, No. 7, Aug. 5, 2014, pp. 565-575, XP055176041, DOI: 10.7897/223-8407.0507115 abstract. p. 565, left-hand column. p. 566, left-hand column, last paragraph-right hand column, paragraph 1, table 4. p. 574, left-hand column, last paragraph.
International Search Report for PCT/US2014/071887 dated Mar. 23, 2015.
Krishna et al. ("Krishna", 2010, Indian Coconut Journal, 15-27).
Lu B et al: "Racecadotril dropping pill for curing acute diarrhea, is prepared from racecadotril and carrier comprising polyethylene glycol and polyoxystearate 40", WPI/Thompson., vol. 2008, No. 79.
Liao A: "Racecadotril liposome solid preparation comprises racecadotril, soya bean lecithin, hydrogenated egg lecithin, cholesterol, and Tween 80", WPI/Thomson., vol. 2011, No. 64, Jul. 27, 2011, XP002712507, the whole document.
Matheson AJ, Noble S (Apr. 2000). "Racecadotril". Drugs 59 (4): 829-35; discussion 836-7.
Diarrhoea: why children are still dying and what can be done, The United Nations Children's Fund, World Health Organization, 2009.
Diarrhoeal Disease Fact Sheet N° 330, World Health Organization, Apr. 2013.
Dupont, H.L., Acute infectious diarrhea in immunocompetent adults, New England Journal of Medicine, 2014, 370:1532-40.
Allen S.J., et al., Probiotics for treating acute infectious diarrhoea (Review), Cochrane Database of Systematic Reviews 2010, Issue 11. Art. No. CD003048. DOI: 10.1002/14651858.CD003048.pub3.
Schwartz J.C., Int. Antimicrob. Agents, 2000, 14, 81.
Lecomte et al., Int. J. Antimicrob. Agents, 2000, 14, 81.
S. Setthacheewakul et al. " European Journal of Pharmaceutics and Biopharmaceutics". vol. 76 (2010) pp. 475-485.
USP 24 (United States Pharmacopeia 24, United States Pharmacopeia Convention, Inc., Rockville, MD). pp. 1940-1943.
International Search Report for PCT/US2015/044296 dated Mar. 22, 2016.

* cited by examiner

RACECADOTRIL LIPID COMPOSITIONS

This application claims priority of the benefit of the filing of U.S. Provisional Application Ser. No. 61/787,597, filed Mar. 15, 2013, the contents of which are hereby incorporated by reference in their entirety.

BACKGROUND OF THE INVENTION

Field of the Invention

The present invention relates to lipid/microemulsion compositions. More particularly, the present invention relates to lipid/microemulsion compositions containing a pharmaceutical active ingredient and the method of making said compositions.

Related Background Art

Diarrhea is an intestinal disorder that is characterized by an increase in the frequency of watery bowel movements. It may result from a variety of causes including bacteria or viral induced diarrhea. Food intolerance caused by allergy or the consumption of foods such as fatty or spicy foods may result in diarrhea. Food poisoning may also lead to diarrhea. In some instances, diarrhea may be a symptom of other conditions and diseases.

Diarrhea is symptomatic of an intestinal or other bodily function disorder. Various prescription and nonprescription products can be taken for relief. However, many of these products provide relief with some side effects.

Racecadotril is also used in the treatment of diarrhea. It reduces (i) hypersecretion of water and electrolytes into the intestinal lumen, (ii) the incidence and duration of acute diarrhea and (iii) diarrhea-associated symptoms.

Racecadotril is a pharmaceutical active ingredient that exhibits poor solubility and poor oral bioavailability. Presently, racecadotril is available in solid oral dosage forms.

SUMMARY OF THE INVENTION

The present invention is directed to a microemulsion composition comprising racecadotril, at least one surfactant and a lipid.

In one embodiment, the inventive microemulsion composition comprises about 0.01 wt. % to about 24.0 wt. % racecadotril, about 1 wt. % to about 95 wt. % of surfactant in total, and about 0.01 wt. % to about 60 wt. % lipid, wherein each wt. % is based upon 100 ml of the composition.

The present invention also includes a method for treating a subject experiencing diarrhea comprising the step of orally administering to the subject a composition comprising racecadotril, at least one surfactant, and a lipid.

DETAILED DESCRIPTION OF THE INVENTION

As used herein, a "microemulsion" refers to a liquid mixture of a lipid, water and at least one surfactant. A microemulsion is characterized by its clear, thermodynamically stable, and isotropic appearance.

As used herein, "stable" refers to a composition that is clear to the naked eye and substantially free of chemical degradation of racecadotril, substantial color change, turbidity or oily globules. No phase separation should be observed in either aqueous and/or non-aqueous components for at least about 3 months at 40° C. More preferably, no phase separation should be observed in either aqueous and/or non-aqueous components for at least about 6 months at 40° C. In one embodiment, the total chemical degradant products of racecadotril should be less than 0.5 percent by weight (wt. %), e.g. less than 0.2 wt. % based on the total wt. % of racecadotril when stored at 3 months and 40° C. In another embodiment, the total chemical degradant products of racecadotril should be less than 0.5 percent by weight (wt. %), e.g. less than 0.2 wt. % based on the total wt. % of racecadotril when stored at 6 months and 40° C.

As used herein, "self-microemulsifying drug delivery systems" (SMEDDS) are mixtures of oils, surfactants, and sometimes cosolvents. SMEDDS can be used for formulating systems to improve the oral absorption of highly lipophilic compounds. SMEDDS emulsify spontaneously using gentle agitation to produce fine oil-in-water emulsions when introduced into an aqueous phase. A drug in an SMEDDS appears in a small droplet size and exhibits increased dissolution and permeability. SMEDDS may be formulated for liquid or solid use. For solid use, the solids are packaged in capsules or tablets. Liquid filled or semi-solid filled capsules are a preferred dosage form by certain consumers, due to the perception of speed, visual appearance of the drug composition and ease of swallowing.

The present invention is a microemulsion composition comprising racecadotril, at least one surfactant, and a lipid.

Various studies have shown racecadotril to be efficacious in reducing the symptoms of diarrhea. One benefit of using racecadotril over other remedies is that racecadotril has been shown to have fewer side effects such as post-treatment constipation.

Racecadotril has low water solubility of about 10 micrograms/ml at room temperature conditions. In the inventive composition, the racecadotril may be solubilized in the microemulsion.

Racecadotril is included in the microemulsion composition in an amount from about 0.01 wt. % to about 24.0 wt. % per 100 ml of the emulsion composition. Preferably, the racecadotril is about 0.01 wt. % to about 18.0 wt. %, and more preferably, about 0.01 wt. % to about 12.0 wt. % per 100 ml of the emulsion composition, and even more preferably, about 0.01 wt. % to about 10.0 wt. % per 100 ml of the emulsion composition. In one embodiment, the racecadotril is about 4.0 wt. % to about 24.0 wt. % per 100 ml of the emulsion composition. In another embodiment, the racecadotril is about 4.0 wt. % to about 18.0 wt. % per 100 ml of the emulsion composition. In yet another embodiment, the racecadotril is about 4.0 wt. % to about 12.0 wt. % per 100 ml of the emulsion composition. In still yet another embodiment, the racecadotril is about 4.0 wt. % to about 10.0 wt. % per 100 ml of the emulsion composition.

The inventive microemulsion composition includes at least one surfactant. The surfactant may be, for example, a nonionic surfactant, cationic surfactant, anionic surfactant, or mixtures thereof.

Suitable surfactants include, for example, water-insoluble surfactants having a hydrophilic-lipophilic balance (HLB) value less than 12 and water-soluble surfactants having a HLB value greater than 12. Surfactants that have a high HLB and hydrophilicity, aid the formation of oil-water droplets. The surfactants are amphiphilic in nature and are capable of dissolving or solubilizing relatively high amounts of hydrophobic drug compounds.

Non-limiting examples, include, Tween, Dimethylacetamide (DMA), Dimethyl sulfoxide (DMSO), Ethanol, Glycerin, N-methyl-2-pyrrolidone (NMP), PEG 300, PEG 400, Poloxamer 407, Propylene glycol, Phospholipids, Hydrogenated soy phosphatidylcholine (HSPC), Distearoylphosphatidylglycerol (DSPG), L-α-dimyristoylphosphatidylcholine (DMPC), L-α-dimyristoylphosphatidylglycerol (DMPG), Polyoxyl 35 castor oil (CREMOPHOR EL, CREMOPHOR ELP), Polyoxyl 40 hydrogenated castor oil (Cremophor RH 40), Polyoxyl 60 hydrogenated castor oil (CREMOPHOR RH 60), Polysorbate 20 (TWEEN 20), Polysorbate 80 (TWEEN 80), d-α-tocopheryl polyethylene glycol 1000 succinate (TPGS), Solutol HS-15, Sorbitan monooleate (SPAN 20), PEG 300 caprylic/capric glycerides (SOFTIGEN 767), PEG 400 caprylic/capric glycerides (LABRASOL), PEG 300 oleic glycerides (LABRAFIL M-1944CS), Polyoxyl 35 Castor oil (ETOCAS 35), Glyceryl Caprylate (Mono- and Diglycerides) (IMWITOR), PEG 300 linoleic glycerides (LABRAFIL M-2125CS), Polyoxyl 8 stearate (PEG 400 monosterate), Polyoxyl 40 stearate (PEG 1750 monosterate), Peppermint oil, and combinations thereof.

Additionally, suitable surfactants include, for example, polyoxyethylene derivative of sorbitan monolaurate such as polysorbate, caprylcaproyl macrogol glycerides, polyglycolyzed glycerides, and the like.

In one embodiment, the surfactant is a combination of polyoxyl 35 castor oil and glyceryl caprylate (mono- and diglycerides) NF.

In the inventive composition, the total weight percent of surfactant(s) is from about 1 wt. % to about 95 wt. % per 100 ml of the microemulsion composition. Preferably, the surfactant is about 25 wt. % to about 95 wt. %, and more preferably, about 30 wt. % to about 90 wt. % per 100 ml of the microemulsion composition. In one embodiment, the surfactant is about 45 wt. % to about 95 wt. % per 100 ml of the microemulsion composition.

A lipid is another essential component of the inventive composition. The lipid aids in solubilizing the racecadotril and also facilitates the self-emulsification process. Suitable lipids include, for example, vegetable oils (modified and/or hydrolyzed), long-chain triglycerides and medium-chain triglycerides having different degrees of saturation, and combinations thereof may be used.

In addition, monoglyceride, diglyceride, and/or triglyceride emulsifiers (fats and oils) that are lipophilic and insoluble in water (available from Abitec Corporation, sold under the tradename CAPMUL®) may be used as the lipid. For example, Beeswax, Oleic acid, Soy fatty acids, d-α-tocopherol (Vitamin E), Corn oil mono-di-tridiglycerides, Medium chain (C8/C10) mono- and diglycerides, Long-chain triglycerides, Castor oil, Corn oil, Cottonseed oil, Olive oil, Peanut oil, Peppermint oil, Safflower oil, Sesame oil, Soybean oil, Hydrogenated soybean oil, Hydrogenated vegetable oils, Medium-chain triglycerides, Caprylic/capric triglycerides derived from coconut oil, palm seed oil, and combinations thereof.

The lipid is included in the composition in an amount from about 0.01 wt. % to about 60 wt. % per 100 ml of the emulsion composition. Preferably, the lipid is about 0.01 wt. % to about 50 wt. %. In another embodiment, the lipid is about 1 wt. % to about 20 wt. % per 100 ml of the emulsion composition, more preferably, about 1 wt. % to about 15 wt. % per 100 ml of the emulsion composition, and even more preferably, about 1 wt. % to about 10 wt. % per 100 ml of the emulsion composition. In one particular embodiment, the lipid is from about 1 wt. % to about 2 wt. % per 100 ml of the emulsion composition.

It is desirable to minimize the amount of water in the composition. The amount of water in the composition will be largely determined by the water content of each component that is included in the composition. In one embodiment, the water content of the composition is less than about 3.5 wt. % based on the total wt. % of the composition. In another embodiment, the water content of the composition is less than about 2.5 wt. % based on the total wt. % of the composition. In yet another embodiment, the water content of the composition is less than about 0.5 wt. % based on the total wt. % of the composition. In still yet another embodiment, the water content of the composition is less than about 0.2 wt. % based on the total wt. % of the composition.

Optionally, a variety of ingredients may be included in the emulsion composition of the present invention.

Any coloring agent suitable for use in a food or pharmaceutical product may be used in the present invention. Typical coloring agents include, for example, azo dyes, quinopthalone dyes, triphenylmethane dyes, xanthene dyes, indigoid dyes, iron oxides, iron hydroxides, titanium dioxide, natural dyes, and mixtures thereof. More specifically, suitable colorants include, but are not limited to patent blue V, acid brilliant green BS, red 2G, azorubine, ponceau 4R, amaranth, D&C red 33, D&C red 22, D&C red 26, D&C red 28, D&C yellow 10, FD&C yellow 5, FD&C yellow 6, FD&C red 3, FD&C red 40, FD&C blue 1, FD&C blue 2, FD&C green 3, brilliant black BN, carbon black, iron oxide black, iron oxide red, iron oxide yellow, titanium dioxide, riboflavin, carotenes, antyhocyanines, turmeric, cochineal extract, clorophyllin, canthaxanthin, caramel, betanin, and mixtures thereof.

Similarly, a flavor may be included in the emulsion composition. The amount of flavor added to the composition is dependent upon the desired taste characteristics.

The composition may contain other ingredients or components, such as aromas; sweeteners such as sucralose, sorbitol, high fructose corn syrup, sugar, and the like; viscosity modifiers such as xanthan gum; preservatives such as sodium benzoate NF, buffers such as citric acid and/or sodium chloride; or mixtures thereof.

The emulsion composition of the present invention may be made by any method known to those skilled in the art so long as it results in the desired composition.

Suitable methods include, for example, combining each ingredient in a mixing kettle, where the ingredients may be added sequentially or in any manner so long as the intended result is achieved. Moreover, the mixing action should be sufficient to incorporate each ingredient into the composition.

The primary means of assessing the stability of the emulsion is based on analytical degradation analysis. The efficiency of self-emulsification could be estimated by determining the rate of emulsification, droplet-size distribution and turbidity measurements.

In addition, stability may be evaluated by measuring the turbidity of the emulsion. This evaluation helps to determine whether the emulsion reaches equilibrium quickly and in a reproducible time.

Stability is also evaluated by checking for oversaturation (precipitation). The test is performed by placing 1 ml of formulation in a beaker with 250 ml of 0.1 N HCL. If a precipitation is formed, then the system is oversaturated.

In one embodiment, of the present invention, the microemulsion composition is administered as a packaged emulsion for direct oral consumption. In another embodiment, the microemulsion composition is administered in an oral soft gelatin capsule containing the microemulsion composition. In yet another embodiment, the microemulsion composition is administered in a multiple of microgel beads containing the microemulsion composition. In still yet another embodiment the microemulsion composition is administered in a hard gelatin capsule containing the microemulsion composition. When the microemulsion composition is contained in the hard gelatin capsule, the hard gelatin capsule may be banded. In still yet another embodiment, the microemulsion composition is administered in a suppository or enema containing the microemulsion composition.

Optionally, the microemulsion composition of the present invention comprises a second active ingredient. In one embodiment the second active ingredient is a digestive health active ingredient. Non-limiting examples, include, for example, laxatives, antacids, proton pump inhibitors, anti-gas agents, antiemetics, H2 blockers, or a second antidiarrheal agent.

In one embodiment, the second active ingredient is incorporated into the microemulsion matrix. In another embodiment, the second active ingredient is present in another portion of the dosage form composition which is separate from the microemulsion composition. In yet another embodiment, the second active ingredient is microencapsulated.

Suitable anti-gas agents include, but are not limited to simethicone.

Suitable additional antidiarrheal agents include, but are not limited to loperamide.

In one embodiment, the inventive microemulsion composition includes about 8.0 wt. % to about 10.0 wt. % racecadotril, about 88 wt. % to about 91 wt. % of surfactant in total, about 1 wt. % to about 2 wt. % lipid, wherein each wt. % is based upon 100 ml of the composition.

In another embodiment, the inventive microemulsion composition includes about 0.01 wt. % to about 24.0 wt. % racecadotril, about 1 wt. % to about 95 wt. % of surfactant in total, about 0.01 wt. % to about 60 wt. % lipid, wherein each wt. % is based upon 100 ml of the composition.

In yet another embodiment, the inventive microemulsion composition includes about 3.0 wt. % to about 7.0 wt. % racecadotril, about 40 wt. % to about 53 wt. % of surfactant in total, about 40 wt. % to about 53 wt. % lipid, wherein each wt. % is based upon 100 ml of the composition.

The inventive microemulsion composition may be delivered in any suitable delivery system. For example, in one embodiment, the microemulsion composition is delivered orally. In another embodiment, the microemulsion composition is delivered in a soft shell dosage form. In still another embodiment, the microemulsion composition is delivered in a hard shell dosage form. In still yet another embodiment, a tablet dosage form is used to deliver the microemulsion composition.

The present invention also includes a method for treating a subject experiencing diarrhea comprising the step of orally administering to the subject a composition comprising racecadotril, at least one surfactant, and a lipid.

The following examples are provided to further illustrate the compositions and methods of the present invention. It should be understood that the present invention is not limited to the examples described.

Example 1

Concentrated Racecadotril Lipid Composition

For Use in Liquid Filled Gelatin Capsule

TABLE 1

Racecadotril Lipid Based Composition as a percentage of the composition: Triglyceride Type 1

| Ingredient | Formula 1 (% w/w) | Formula 3 (% w/w) | Formula 5 (% w/w) |
|---|---|---|---|
| Racecadotril | 9.60 | 9.31 | 8.34 |
| Polyoxyl 35 Castor oil[1] | 79.55 | 52.60 | 27.50 |
| Glyceryl Caprylate (Mono- and Diglycerides) NF[2] | 9.04 | 36.27 | 62.33 |
| Medium Chain Triglycerides[3] | 1.81 | 1.81 | 1.83 |
| Total | 100 | 100 | 100 |
| Racecadotril Assay (mg/mL) | 96.04 | 93.14 | 83.37 |

[1]Commercially available from CRODA Healthcare as ETOCAS ® 35 USP/NF, EP, JP
[2]Commercially available from CREMER as IMWITOR ® 988 USP/NF, EP, JP
[3]Commercially available from CREMER as MIGLYOL ® 810N (Caprylic/Capric Triglycerides; 70:30/C8:C10) USP/NF, EP, JP

TABLE 2

Racecadotril Lipid Based Composition as a percentage of the composition: Triglyceride Type 2

| Ingredient | Formula 2 (% w/w) | Formula 4 (% w/w) | Formula 6 (% w/w) |
|---|---|---|---|
| Racecadotril | 9.47 | 8.98 | 8.33 |
| Polyoxyl 35 Castor oil[1] | 79.67 | 52.79 | 27.50 |
| Glyceryl Caprylate (Mono- and Diglycerides) NF[2] | 9.05 | 36.41 | 62.33 |
| Medium Chain Triglycerides[3] | 1.81 | 1.82 | 1.83 |
| Total | 100 | 100 | 100 |
| Racecadotril Assay (mg/mL) | 94.68 | 89.77 | 83.34 |

[1]Commercially available from CRODA Healthcare as ETOCAS ® 35 USP/NF, EP, JP
[2]Commercially available from CREMER as IMWITOR ® 988 USP/NF, EP, JP
[3]Commercially available from CREMER as MIGLYOL ® 812N (Caprylic/Capric Triglycerides; 60:40/C8:C10) USP/NF, EP, JP Utilizing the materials in Table 1 and Table 2, the following mixing steps were taken to form the microemulsion. A total of 6 mixtures were prepared including 3 ratios, with each prepared with MIGLYOL 810N (Table 1) and MIGLYOL 812N (Table 2).

Step 1: In a suitable vessel, a mixture of the Polyoxyl 35 Castor oil (ETOCAS® 35), Glyceryl Caprylate (IMWITOR® 988) and Medium Chain triglycerides (MIGLYOL® 810N & 812N) was prepared in three separate mixtures in the following weight ratios: 88:10:2 (Ratio 1), 58:40:2 (Ratio 2), and 30:68:2 (Ratio 3).

Step 2: The mixture(s) from Step 1 were mixed utilizing a vortex mixer.

Step 3: The Racecadotril was slowly added to the mixture(s) from Step 2 utilizing the vortex mixer, and mixed for 5 minutes.

Step 4: The mixture from Step 3 was placed into a laboratory shaker and mixed for 36 hours until a clear solution was formed.

Stability of Racecadotril Lipid Formulation

The chemical stability of the formulations prepared in Example 1 was examined for racecadotril degradation when stored for 3 months at 40° C. in sealed bottles, and is shown in Table 3.

TABLE 3

Stability Data of Racecadotril in Lipid-based Solution (3 month @ 40° C.)

| | Formula* | | | | | |
|---|---|---|---|---|---|---|
| | 1 | 2 | 3 | 4 | 5 | 6 |
| Racecadotril (%) | 99.46 | 99.41 | 98.45 | 98.37 | 98.61 | 98.49 |
| Thiorphan (%) | ND | ND | ND | ND | ND | ND |
| Benzyl Alcohol (%) | 0.13 | 0.12 | 0.48 | 0.52 | 0.32 | 0.45 |
| Impurity C (%) | ND | ND | ND | ND | 0.04 | ND |
| Impurity G (%) | 0.01 | 0.02 | 0.02 | 0.02 | 0.02 | 0.02 |
| Solubility. (mg/mL) | 96 | 94.7 | 93.1 | 89.8 | 83.4 | 83.3 |
| Solubility (mg/g)*** | 92.2 | 90.7 | 90.6 | 87.7 | 82.1 | 82.1 |

*: Formula:
1. 88% Super Refined Etocas 35, 10% Imwitor 988, 2% Miglyol 810 N (Ratio 1)
2. 88% Super Refined Etocas 35, 10% Imwitor 988, 2% Miglyol 812 N (Ratio 1)
3. 58% Super Refined Etocas 35, 40% Imwitor 988, 2% Miglyol 810 N (Ratio 2)
4. 58% Super Refined Etocas 35, 40% Imwitor 988, 2% Miglyol 812 N (Ratio 2)
5. 30% Super Refined Etocas 35, 68% Imwitor 988, 2% Miglyol 810 N (Ratio 3)
6. 30% Super Refined Etocas 35, 68% Imwitor 988, 2% Miglyol 812 N (Ratio 3)
ND—Not detectable Ingredient:
A. Super Refined Etocas 35 (NF, EP, JP):
   Manufactured by CRODA Health Care
   Polyoxyl 35 Castor Oil
   HLB value of 14
B. Imwitor 988: Medium Chain Partial Glycerides
   Manufactured by CREMER
   Glyceryl Caprylate (Mono- and Diglycerides)
   Melting Point~25° C.
   HLB value of 4
C. Imwitor 742: Medium Chain Partial Glycerides
   Manufactured by CREMER
   Caprylic/Capric Glycerides
   Melting Point~25° C.
   HLB value of 3-4
D. Miglyol: Medium Chain Triglycerides (MCT Oils, Fractionated Coconut Oil)
   Manufactured by CREMER
   Caprylic (C8)/Capric (C10) Triglycerides
   810N—70:30 C8/C10 blend
   812N—60:40 C8/C10 blend
Conversion based on the density of each formula:
Formula 1/Formula 2: 1.042 g/ml
Formula 3/Formula 4: 1.028 g/ml
Formula 5/Formula 6: 1.016 g/ml
Water Content (% w/w):
   Racecadotril 0.5%
   Super Refined Etocas 0-3% (EP): 0%
   Super Refined Etocas 0-1% (JP): 0%
   Imwitor 988: 0.2%
   Miglyol 810N: 0.01%
   Miglyol 812N: 0.01%

| Formula | Water Content (% w/w) |
|---|---|
| 1 | 0.02 |
| 2 | 0.02 |
| 3 | 0.08 |
| 4 | 0.08 |
| 5 | 0.13 |
| 6 | 0.13 |
| 7 | 0.09 |
| 8 | 0.09 |
| 9 | 0.10 |
| 10 | 0.10 |

Example 2

Concentrated Racecadotril Lipid Composition

For Use in Liquid Filled Gelatin Capsule

TABLE 4

| Ingredient | Formula 7 (% w/w)$^a$ | Formula 8 (% w/w) |
|---|---|---|
| Racecadotril | 4.61 | 4.25 |
| Glyceryl Caprylate (Mono- and Diglycerides) NF[1] | 47.95 | 48.00 |
| Medium Chain Triglycerides[2] | 47.44 | — |
| Medium Chain Triglycerides[3] | — | 47.75 |
| Total | 100 | 100 |
| Racecadotril Assay (mg/mL) | 46.11 | 42.49 |

[1]Commercially available from CREMER as IMWITOR 742 ® USP/NF, EP, JP
[2]Commercially available from CREMER as MIGLYOL ® 810N (Caprylic/Capric Triglycerides; 70:30/C8:C10) USP/NF, EP, JP
[3]Commercially available from CREMER as MIGLYOL ® 812N (Caprylic/Capric Triglycerides; 60:40/C8:C10) USP/NF, EP, JP

TABLE 5

| Ingredient | Formula 9 (51.5:48.5)$^a$ | Formula 10 (51.4:48.6) |
|---|---|---|
| Racecadotril | 5.28 | 5.59 |
| Glyceryl Caprylate (Mono- and Diglycerides) NF[1] | 48.83 | 48.54 |
| Medium Chain Triglycerides[2] | 45.90 | — |
| Medium Chain Triglycerides[3] | — | 45.87 |
| Total | 100 | 100 |
| Racecadotril Assay (mg/mL) | 52.78 | 55.93 |

[1]Commercially available from CREMER as IMWITOR 988 ® USP/NF, EP, JP
[2]Commercially available from CREMER as MIGLYOL ® 810N (Caprylic/Capric Triglycerides; 70:30/C8:C10) USP/NF, EP, JP
[3]Commercially available from CREMER as MIGLYOL ® 812N (Caprylic/Capric Triglycerides; 60:40/C8:C10) USP/NF, EP, JP Testing Methods:
Sample Preparation: (in Acetonitrile)
  1. Pipet 1 mL of Racecadotril lipid solution into a 100 mL volumetric flask (V.F.)
  2. Dilute to volume with Acetonitrile. Add about 20 mL of Dimethylacetamide if necessary.
  3. Further dilute the sample solution to about 0.1 mg/mL with acetonitrile if necessary.
Sample Analysis
  Inject reference standards (0.1 mg/mL of Racecadotril in Acetonitrile) and samples onto a suitable HPLC system under conditions similar to those suggested below. Parameters may be modified to optimize chromatography.
  Determine the assay of Racecadotril using the Racecadotril peak areas of the sample solutions under test in comparison with the Racecadotril peak areas of the standard solution. The degradation products levels are determined by % peak area relative to the Racecadotril peak.

Chromatographic Conditions (European Pharmacopoeia Racecadotril Method):

| Column: | Phenomenex Luna 5 µm C18 (2), 100Å; 250 mm × 4.6 mm ID (Column ID in EP is 4.0 mm) |
|---|---|
| Column heater: | 30° C. |
| Wavelength: | 210 nm |
| Inj. Vol.: | 10 µL |
| Flow rate: | 1 mL/min |

Gradient Table:

| Time (min) | flow | % A | % B |
|---|---|---|---|
| Initial | 1.0 | 60 | 40 |
| 5 | 1.0 | 60 | 40 |
| 25 | 1.0 | 20 | 80 |
| 35 | 1.0 | 20 | 80 |
| 36 | 1.0 | 60 | 40 |
| 45 | 1.0 | 60 | 40 |

Mobil Phase A: Phosphate buffer, pH 2.5 (Buffer prep: dissolve 1 g of potassium dihydrogen phosphate in water, adjust to pH 2.5 with phosphoric acid, dilute to 1000 mL with water)
Mobil Phase B: 100% Acetonitrile While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed:

1. A composition for oral administration, comprising:
   about 4% to about 10% racecadotril, about 90% of at least one surfactant and about 1% to about 2% lipid,
   wherein the at least one surfactant is a glyceride selected from the group consisting of Distearoylphosphatidylglycerol (DSPG), L-α-dimyristoylphosphatidylcholine (DMPC), L-α-dimyristoylphosphatidylglycerol (DMPG), Polyoxyl 35 castor oil, Polyoxyl 40 hydrogenated castor oil, Polyoxyl 60 hydrogenated castor oil, PEG 300 capryliecapric glycerides, PEG 400 caprylic/capric glycerides, PEG 300 oleic glycerides, PEG 300 linoleic glycerides, Glyceryl Caprylate, Glyceryl Caprylate Diglyceride medium chain partial glycerides, and mixtures thereof,
   wherein the lipid is a triglyceride selected from the group consisting of Long-chain triglycerides, Medium-chain triglycerides, Caprylic/capric triglycerides and mixtures thereof;
   wherein the composition is stable for about 3 months at 40° C.

2. The composition of claim 1, wherein the at least one surfactant is present in an amount of from about 88 wt. % to about 91 wt. % in total per 100 ml of the composition.

3. The composition of claim 1, further comprising an optional ingredient selected from the group consisting of buffers, preservatives, sweeteners, viscosity modifiers, colors, aromas, flavors, and mixtures thereof.

4. The composition of claim 1, further comprising an optional ingredient selected from the group consisting of xanthan gum, citric acid, sodium benzoate, sucralose, flavors and mixtures thereof.

5. The composition of claim 1, wherein the composition has a total water content of less than about 3.5 wt. % based on the total weight of the composition.

6. The composition of claim 1, wherein the at least one surfactant is castor oil.

7. The composition of claim 1, wherein the at least one surfactant is selected from a monoglyceride and a diglyceride.

8. The composition of claim 1, further comprising a digestive health active ingredient.

9. The composition of claim 8, wherein the digestive health active ingredient is selected from the group consisting of laxatives, antacids, proton pump inhibitors, anti-gas agents, antiemetics, H2 blockers, and antidiarrheal agents.

10. The composition of claim 8, wherein the anti-gas agent is simethicone.

11. The composition of claim 8, wherein the antidiarrheal agent is loperamide.

12. A soft shell dosage form comprising the composition of claim 1.

13. A hard shell dosage form containing the composition of claim 1.

14. A tablet dosage form containing the composition of claim 1.

15. A method for treating a subject experiencing diarrhea comprising the step of orally administering to the subject the composition of claim 1.

* * * * *